United States Patent
Hanson et al.

(10) Patent No.: US 9,358,378 B2
(45) Date of Patent: Jun. 7, 2016

(54) DUAL RESERVOIR IMPLANTABLE ACCESS PORT

(71) Applicant: AngioDynamics, Inc., Latham, NY (US)

(72) Inventors: Barry G. Hanson, Thomaston, GA (US); Brian Keese, Molena, GA (US); Blaine Johnson, Midvale, UT (US); Daniel K. Recinella, Queensbury, NY (US); Michael Fowler, Fayetteville, GA (US); A. David Smith, Rockwall, TX (US); James Steven Kenny, Queensbury, NY (US)

(73) Assignee: Angio Dynamics, Inc., Latham, NY (US)

( * ) Notice: Subject to any disclaimer, the term of this patent is extended or adjusted under 35 U.S.C. 154(b) by 112 days.

(21) Appl. No.: 14/159,079

(22) Filed: Jan. 20, 2014

(65) Prior Publication Data

US 2014/0236105 A1      Aug. 21, 2014

Related U.S. Application Data

(63) Continuation of application No. 12/246,303, filed on Oct. 6, 2008, now abandoned.

(60) Provisional application No. 61/056,920, filed on May 29, 2008, provisional application No. 61/044,752, filed on Apr. 14, 2008, provisional application No. 60/977,736, filed on Oct. 5, 2007.

(51) Int. Cl.
*A61M 37/00*      (2006.01)
*A61M 39/02*      (2006.01)

(52) U.S. Cl.
CPC ... *A61M 39/0208* (2013.01); *A61M 2039/0211* (2013.01); *A61M 2039/0232* (2013.01); *A61M 2039/0238* (2013.01)

(58) Field of Classification Search
CPC ............... A61M 39/0208; A61M 2039/0211; A61M 2039/0238; A61M 2039/0229
See application file for complete search history.

(56) References Cited

U.S. PATENT DOCUMENTS

| 6,086,555 | A | * | 7/2000 | Eliasen et al. | 604/93.01 |
| 2006/0100592 | A1 | * | 5/2006 | Eliasen | A61M 39/0208 604/288.02 |
| 2006/0178648 | A1 | * | 8/2006 | Barron et al. | 604/288.02 |

\* cited by examiner

*Primary Examiner* — Emily Schmidt
(74) *Attorney, Agent, or Firm* — Zachary F. Madonna

(57) ABSTRACT

An implantable access port for use in transferring fluid transdermally between an external fluid storage or dispensing device and a site within a patient is disclosed. The access port includes a body, at least two reservoirs defined within the access port body, and at least one septum secured to the body and enclosing the reservoirs within the body. The access port also includes reservoir outlets defined within the reservoirs. The access port also has body conduits defined within the body and in fluid communication with the reservoir outlets and external openings defined in the exterior of the body. An implantable access port and system for use in apheresis is also provided that includes an implantable access port, at least one needle, and a catheter that is fluidly connected to the access port.

9 Claims, 17 Drawing Sheets

343

DUAL RESERVOIR IMPLANTABLE ACCESS PORT

CROSS REFERENCE TO RELATED APPLICATIONS

This application is a continuation of U.S. patent application Ser. No. 12/246,303, which was filed on Oct. 6, 2008, which claims priority to U.S. Provisional Patent Application Ser. No. 60/977,736, which was filed on Oct. 5, 2007, U.S. Provisional Patent Application Ser. No. 61/044,752, which was filed on Apr. 14, 2008, and U.S. Provisional Patent Application Ser. No. 61/056,920, filed May 29, 2008, which applications are incorporated in their entirety in this document by reference.

FIELD OF THE INVENTION

The invention relates in general to medical devices. More particularly, the invention relates to a dual reservoir implantable access port for use in accessing either the vasculature or a selected treatment site within the body of a patient.

BACKGROUND OF THE INVENTION

The use of implantable access ports in the art of drug therapy is well known, in which an access port is implanted beneath the subcutaneous layers of a patient's skin. The known access ports are constructed to provide for repeated access to the vascular system of a patient, or a selected treatment site within the patient's body. The use of these devices reduces the trauma otherwise associated with multiple punctures of the skin, or the inconvenience of an externalized catheter for patient treatment purposes. For example, implantable access ports are used to facilitate frequent blood sampling, or to provide for the delivery of medications, nutritions, blood products, and imaging solutions into the patient's blood stream, or to a desired treatment site within the patient. Access to the implanted access port is typically accomplished by percutaneous needle insertion through the patient's skin into the access port through a penetrable septum or other similar structure by using a non-coring hypodermic needle.

Implantable access ports can also be used for apheresis, an extracorporeal procedure in which the blood of a donor or patient is passed through an apparatus that filters or separates out one or more components of the blood that contribute to a disease state and returns the remainder of the blood to the patient's blood circulation. Invasive apheresis treatments typically are administered frequently and can be painful as a result of the multiple venous punctures to the patient's skin. In order to most effectively perform apheresis procedures, the access ports should be capable of producing adequate blood flow rates and accommodating appropriately sized needles and catheters.

Implantable access ports are supplied as sterile devices, are generally provided for single patient use only, and can be available in a variety of port materials, including polysulfone, acetal plastic and titanium. Available catheter materials can comprise, without limitation, polyurethane and silicone. Suture holes are typically formed in the access port as a part of the base portion thereof and are used to facilitate the anchorage of the access port to the patient's underlying fascia, for example muscle. Implantable access ports are available in single, dual, and low profile models, and are available with attachable, or attached catheters. Implantable access ports are also currently available as power injectable ports for use in, for example, computed tomography ("CT") scanning processes.

Dual model implantable access ports are comprised of two distinct fluid reservoirs contained within a single casing. These devices are useful when a health care provider needs to perform multiple functions that cannot be performed using a typical single reservoir model access port, for example to withdraw blood and administer medication via separate reservoirs. In conventional dual model access ports, each of the fluid reservoirs is circular in shape. This arrangement, however, leads to an increase in size of the geometric footprint of the access port because of the space created between the two circular reservoirs.

What is needed, therefore, is a dual model implantable access port that reduces the size of the geometric footprint of the access port, thereby reducing the size of incision necessary to implant the device in a patient, reducing patient discomfort and other potential medical complications. What is also needed is a dual reservoir implantable access port with a minimal geometric footprint that produces adequate blood flow rates for the performance of apheresis procedures, which can reduce trauma to patients and improve patient outcomes.

SUMMARY OF THE INVENTION

The present invention is an implantable access device for allowing repeated access to, and for use in transferring a fluid transdermally between an external fluid storage or dispensing device and a site, space, device, or other object, fluid, tissue or region within the body of a patient, and which access port overcomes some of the design deficiencies of known access ports and systems used for apheresis.

According to one embodiment, an implantable access port comprises a body comprising at least two reservoirs, at least one septum configured for enclosing each of the reservoirs, and a retainer for securing the septum to the body. In a further embodiment, the access port comprises a body, two D-shaped reservoirs defined within the body, at least one septum secured to the body and adapted to sealingly enclose the reservoirs, and two body conduits defined within the body that are in communication with the reservoir outlets and extend to, and are in communication with, a pair of ports defined in the side wall of the body. The pair of ports are further constructed and arranged to be placed in sealed fluid communication with an outlet stem.

According to various embodiments of the present invention, the D-shaped fluid reservoirs are axially aligned such that the space between the reservoirs is reduced, thereby reducing the overall size and geometric footprint of the implantable access port device. Thus, the size of the incision required to insert the device into a patient can be reduced.

In a further aspect, the vascular access port disclosed herein is used for apheresis and is part of a system or kit that also includes at least one needle and is connected to a catheter.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate embodiments of the invention and together with the description, serve to explain the principles of the invention.

DETAILED DESCRIPTION OF THE INVENTION

Figure 1A:
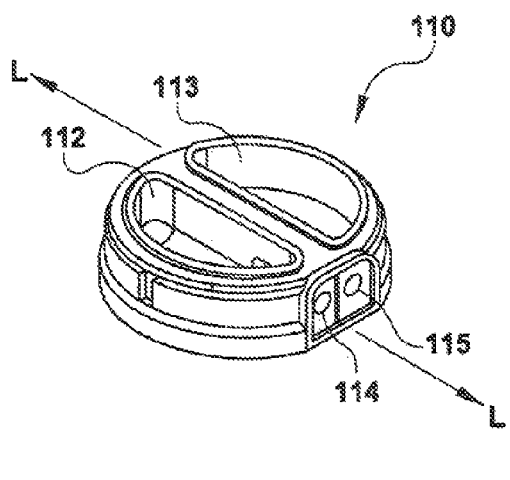
FIG. 1A is a perspective view of a body of an implantable access port having dual D-shaped reservoirs formed therein, according to one embodiment of the present invention.

The present invention may be understood more readily by reference to the following detailed description and the examples included therein and to the Figures and their previous and following description.

Before the systems, devices, and/or methods are disclosed and described, it is to be understood that the systems, devices, and/or methods are not limited to specific methods as such may, of course, vary. It is also to be understood that the terminology used herein is for the purpose of describing particular embodiments only and is not intended to be limiting.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not. In the present invention, "D-shaped" can mean semi-circular, partially circular, semi-elliptical, partially elliptical, kidney-shaped, crescent-shaped, tear-drop shaped with at least one substantially straight portion (e.g., semi-heart shaped), or any other shape comprising a straight portion and an arcuate or curved portion.

Reference is now made, in detail, to the drawings, in which like reference numerals indicate like parts or elements throughout the several views. As illustrated in the Figures, an implantable access port 100 is illustrated having a body 110, a retainer 120, an outlet stem 130, a septum 150, a locking sleeve 160 and a gasket 170. It will be appreciated that the implantable access port, according to various embodiments, can comprise some or all of these components.

For example, in one embodiment, an implantable access port is provided for use in transferring fluid transdermally between an external fluid storage or dispensing device and a site within a patient's body. In another embodiment, the access port can be used for performing apheresis procedures. In these embodiments, the access port can comprise a body, a retainer, and a septum. The body can further have an upper surface, a lower surface and a side wall extending therebetween the upper and lower surfaces. Optionally, at least portions of the respective upper and lower surfaces of the body can be substantially planar.

In one embodiment, the body comprises a first reservoir that is defined therein a portion of the upper surface of the body. The first reservoir extends thereinto the body and has a first reservoir wall. In this aspect, at least a portion of the first reservoir wall can be smooth surfaced. Likewise, a second reservoir can be defined therein a second portion of the upper surface of the body. The second reservoir extends thereinto the body and has a second reservoir wall. In this aspect, at least a portion of the second reservoir wall can be smooth surfaced.

In a further aspect, a pair of ports can be defined therein the side wall of the body. In yet another aspect, a first body conduit can be provided that extends between the first reservoir and a first port of the pair of ports of the body, and is thus in fluid communication with the first reservoir and the exterior of the body. A second body conduit can likewise be provided that extends between the second reservoir and a second port of the pair of ports of the body, and is thus in fluid communication with the second reservoir and the exterior of the body.

Figure 1B:
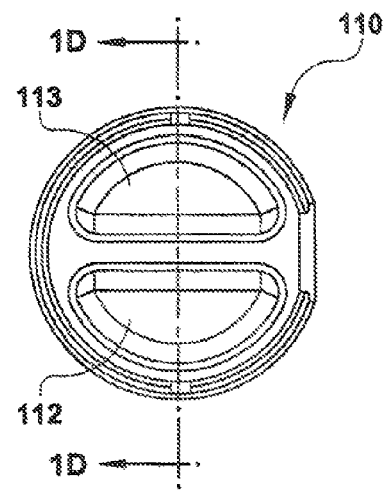
FIG. 1B is a top plan view of the body of FIG. 1A.

As described above, the body 110 of an access port 100, according to various embodiments of the present invention, comprises a plurality of reservoirs, which includes at least a first reservoir and a second reservoir. For example, and as exemplarily as illustrated in FIGS. 1A and 1B, a body can comprise first and second reservoirs, 112 and 113. Each reservoir is defined therein and extends therein the upper surface of the body, and has a reservoir wall surface and a reservoir base 116, as illustrated in FIG. 1D. In one aspect, the reservoir base is substantially perpendicular to at least a portion of the reservoir wall surfaces of the respective first and second reservoirs. In one exemplary aspect, the first and second reservoirs can have a substantially D-shape.

In a further aspect, a portion of the reservoir wall surface of each respective first and second reservoir forms a common wall. In a further aspect, it is contemplated that at least a portion of the common wall can extend substantially along a longitudinal axis of the body. In yet another aspect, at least a portion of the common wall can extend substantially normal to the upper surface of the body.

It is also contemplated that at least a portion of the common wall can extend substantially parallel to the respective first and second body conduits. Optionally, at least a portion of the first and second body conduits can be defined therein a portion of the common wall.

In one embodiment, the D-shaped reservoirs are defined within the body such that they are spaced about the longitudinal axis of the body (such as shown in the top plan view of FIG. 1B). It is contemplated that each of the dual D-shaped reservoir can be of a different size or shape, such as, for example, symmetrical, non-symmetrical, or of different durometers, widths, and heights. According to various embodiments, by aligning the D-shaped reservoirs (regardless of whether they are symmetrical, or similarly sized or shaped) relative to the longitudinal axis of the body, the total width of the access port can be significantly reduced (i.e., the distance measured across both reservoirs).

In this aspect and as one will appreciate, each D-shaped first and second reservoirs comprise a substantially straight wall portion and a substantially arcuate wall portion in the cross-section. In a further aspect, the first and second reservoirs are defined within the body with the respective straight wall portions parallel to and spaced from a plane bisecting the longitudinal axis or center of the body at a predetermined distance. As one will appreciate, at least a portion of the respective straight wall portion of the first and second D-shaped reservoirs form the common wall.

Figure 8:
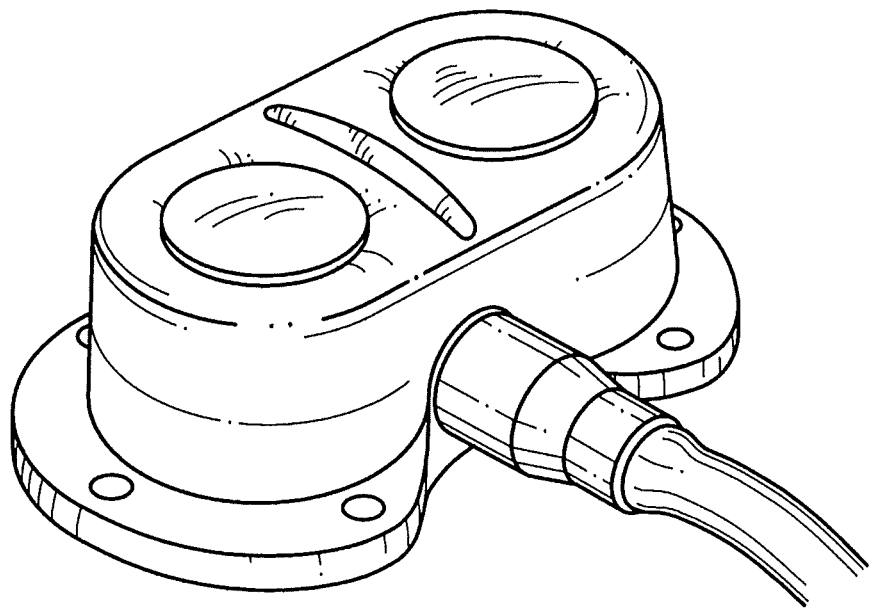
FIG. 8 illustrates a prior art dual reservoir implantable access port comprising two, side-by-side circular reservoirs.

For example and not intended to be limiting, the width of the exemplified dual D-shaped reservoir access port can range from about 1 inch to about 1.3 inches. In a further embodiment, the width can range from about 1.1 to 1.2 inches, such as approximately 1.15 inches. In a particular embodiment, the width is approximately 1.146 inches. Widths of known access ports generally exceed 1.6 inches. Accordingly, as taught herein, the geometric footprint of the dual reservoir access port is reduced compared to the geometric footprint of known dual reservoir access ports, such as that illustrated in FIG. 8. This design is beneficial during apheresis because it reduces the trauma to the patient during the apheresis procedure by having a smaller geometric footprint, and the reservoir design is beneficial because it allows access of large needles into the reservoir during apheresis.

In another embodiment, and as best illustrated in FIG. 1D, the reservoir side walls of the respective first and second reservoirs extend therefrom the reservoir base 116 such that there are no angular corners or junctions formed where the reservoir wall surface joins the reservoir base. In this fashion, there are no defined angular corners or junctions that can in turn lead to the occlusion of blood or other substances in the reservoir as these fluids are passed into or drawn from out of the access port.

Figure 7A:
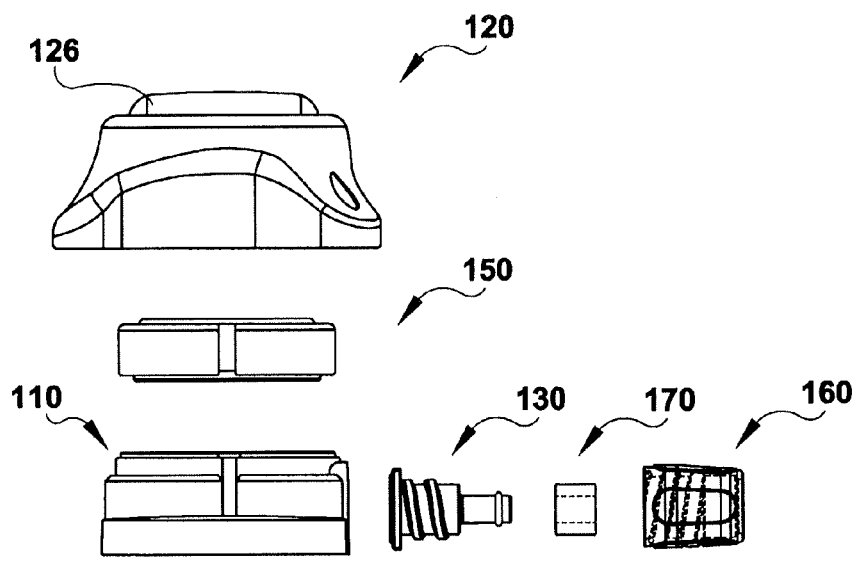
FIG. 7A is a side elevational view of an embodiment of an implantable access port, shown in a disassembled condition, according to one embodiment of the present invention.
Figure 7B:
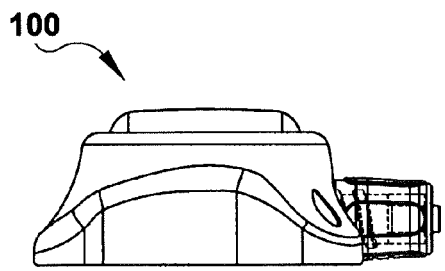
FIG. 7B is a side elevational view of an embodiment of an implantable access port, shown in an assembled condition, according to one embodiment of the present invention.
Figure 7C:
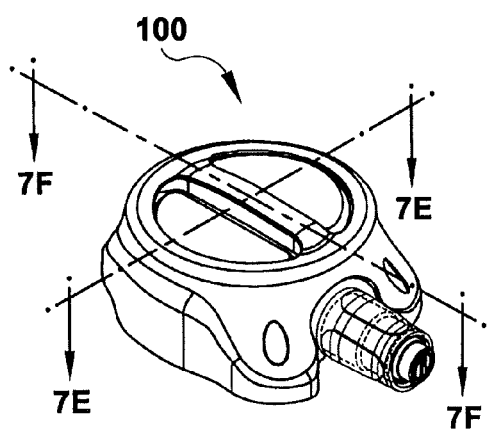
FIG. 7C is a perspective view of an embodiment of an implantable access port, shown in an assembled condition, according to one embodiment of the present invention.
Figure 7D:
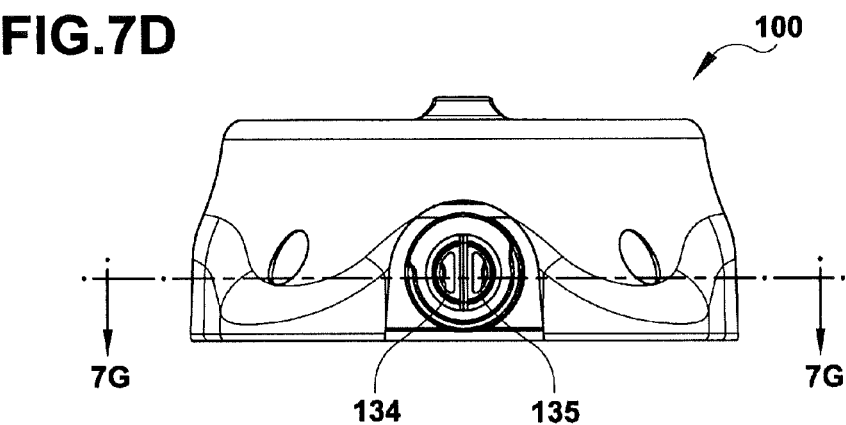
FIG. 7D is a front elevational view of an embodiment of an implantable access port, shown in an assembled condition, according to one embodiment of the present invention.
Figure 7E:
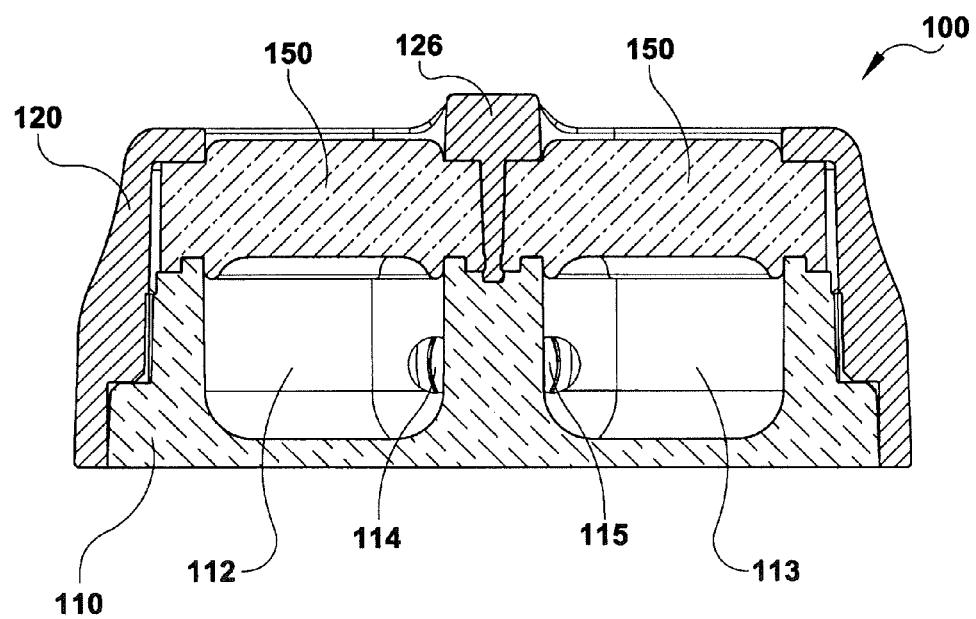
FIG. 7E is a front cross-sectional view, taken along line A-A of FIG. 7C, of an embodiment of an implantable access port, shown in an assembled condition, according to one embodiment of the present invention.

Referring to FIGS. 1A and 7E, a first and second port of the pair of ports are defined within the side wall of the body 110 and, thus, are in fluid communication with respective first and second reservoirs 112 and 113. In one aspect, the first and second ports are in fluid communication with the respective first and second reservoirs via the respective first and second body conduits, 114 and 115, such as shown in FIG. 7G.

In a particular embodiment, a portion of each body conduit is defined in a portion of the respective reservoir. In one aspect, a portion of each body conduit is defined in a portion of reservoir wall surface proximate a point where the upright portion of the reservoir wall surface, the curved portion of the reservoir side surface, and the reservoir base meet. As described above, in one aspect, the reservoir side surface can be substantially smooth-surfaced and thus the "corner" at which juncture of the respective surfaces can be substantially rounded. In this aspect, it is not contemplated that the juncture be limited to an angular corner. In this embodiment, a flow path is provided within the reservoir that cleanly flushes the reservoir as the respective body conduit extends from a "corner" of the reservoir and thus can provide improved flushing of the reservoir.

Figure 2B:
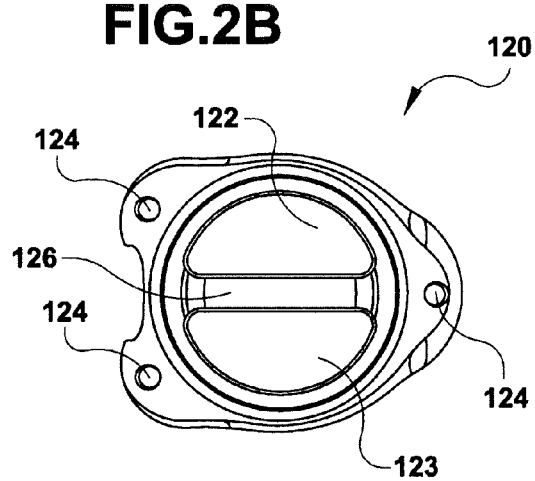
FIG. 2B is a top plan view of the retainer of FIG. 2A.
Figure 2A:
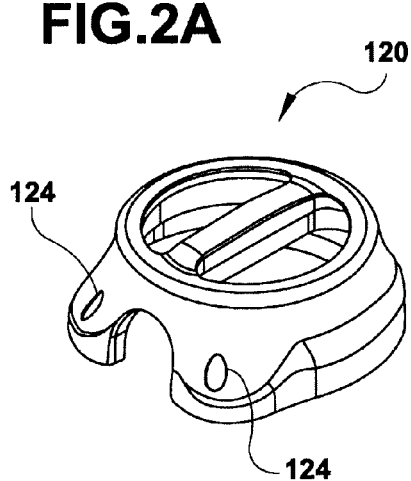
FIG. 2A is a perspective view of a retainer of an implantable access port having a protrusion that divides the retainer access opening into two D-shaped sections, according to one embodiment of the present invention.

Referring now to FIGS. 2A-2C and FIG. 7A, in one embodiment the access port retainer 120 is configured to fixedly mount thereon portions of the body 110. In a further embodiment, the retainer is configured to seal the at least one septum therebetween portions of the retainer and portions of the body. As illustrated in FIGS. 2A and 2B, a retainer can define at least one retainer opening extending therethrough the retainer. In a further embodiment, the retainer can define first and second retainer openings such that when the retainer is operatively mounted thereon the body, the first retainer opening substantially overlies the first reservoir, and the second retainer opening substantially overlies the second reservoir. In one aspect, the first and second retainer openings are separated by a common dividing member. In this aspect, it is contemplated that the first and second openings can be D-shaped openings 122 and 123 separated by the dividing member 126. In one aspect, the retainer can be configured such that the dividing member is formed to substantially overlie the common wall formed by the first and second reservoirs of the body.

Figure 2C:
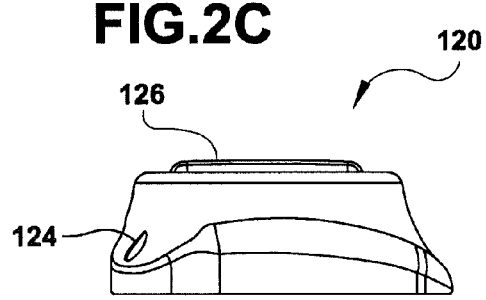
FIG. 2C is a side elevational view of the retainer of FIG. 2A.

In one embodiment, an upper surface of the dividing member can be substantially co-planar with a top surface of the periphery of the retainer. Optionally, as illustrated in FIG. 2C, at least a portion of the dividing member 126 can be raised above (i.e., protrude outwardly from) a plane defined by the periphery of the retainer.

Optionally, the retainer, according to a further embodiment, can comprise one or more suture holes 124 as illustrated in FIG. 2B. So provided, the access port can be sewn to the fascia of a patient by passing appropriate sutures through the suture holes to fasten the access port to the underlying muscle and/or tissues of the patient.

Figure 1C:
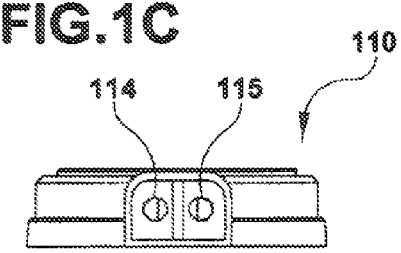
FIG. 1C is a front elevational view of the body of FIG. 1A.
Figure 1D:
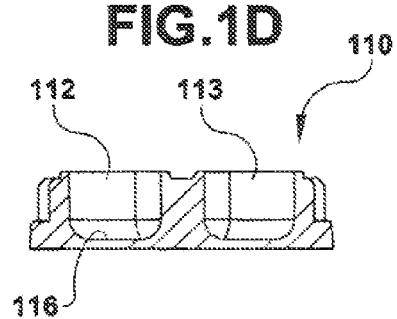
FIG. 1D is a side elevational view, in cross section, of the body of FIG. 1A taken along line A-A of FIG. 1B.
Figure 7F:
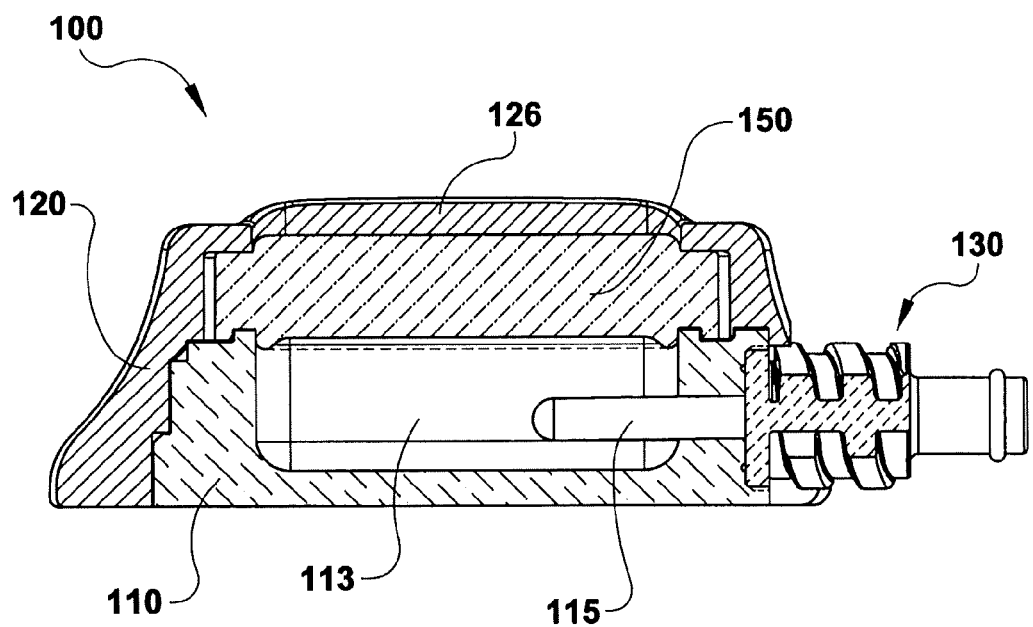
FIG. 7F is a side cross-sectional view, taken along line B-B of FIG. 7C, of an embodiment of an implantable access port, shown in an assembled condition, according to one embodiment of the present invention.
Figure 7G:
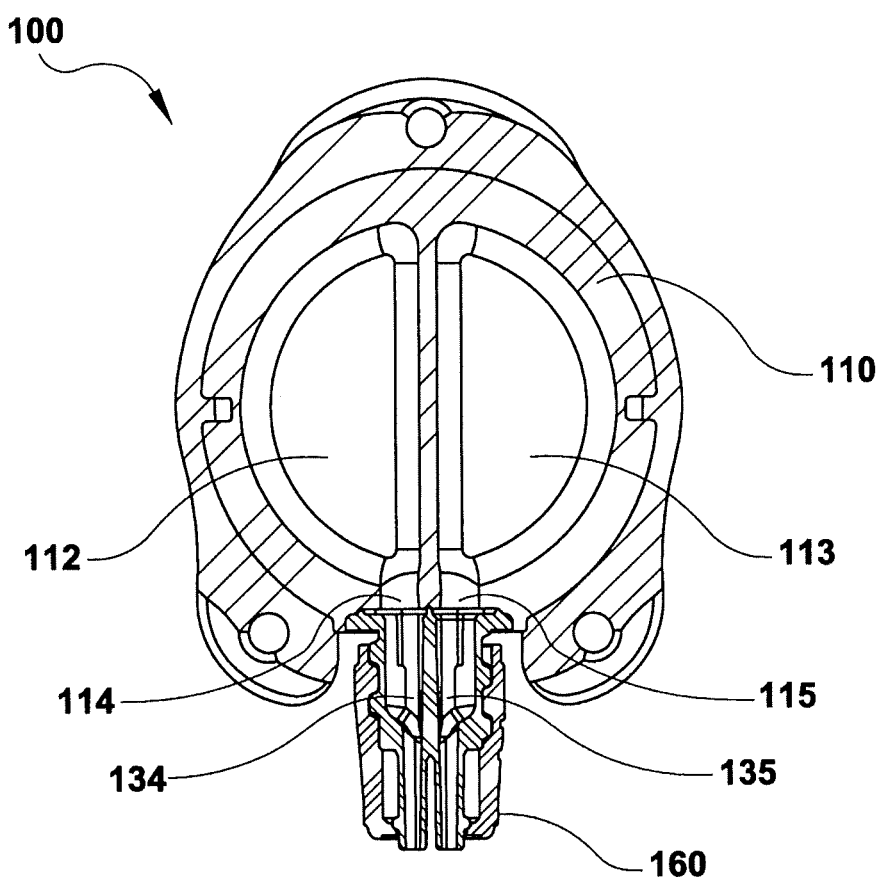
FIG. 7G is a top cross-sectional view, taken along line A-A of FIG. 7D, of an embodiment of an implantable access port, shown in an assembled condition, according to one embodiment of the present invention.

As illustrated in FIGS. 1C, 7F and 7G, the access port body 110 is configured to matably receive an outlet stem 130 such that the outlet stem is placed into fluid communication with the pair of ports in the exterior side wall of the access port body, and thus into fluid communication with the respective first and second reservoirs 112 and 113 through the respective first and second body conduits 114 and 115.

Figure 3A:
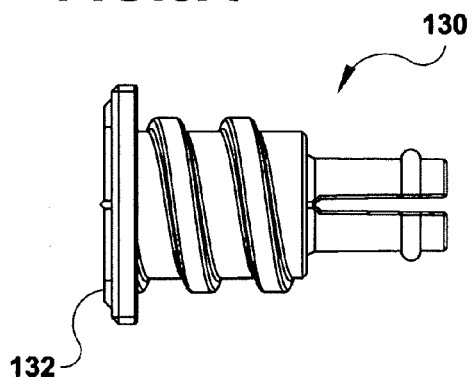
FIG. 3A is top view of an outlet stem of an implantable access port, according to one embodiment of the present invention.
Figure 3B:
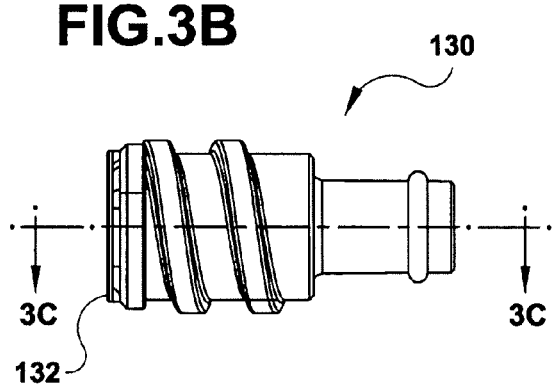
FIG. 3B is a side elevational view of the outlet stem of FIG. 3A.
Figure 3D:
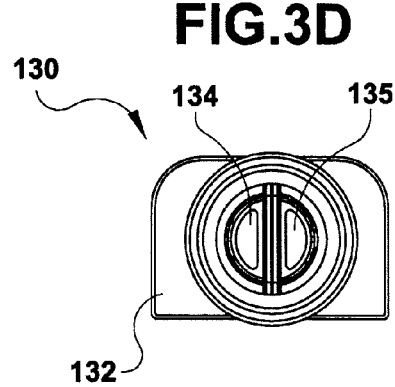
FIG. 3D is a front view of the outlet stem of FIG. 3A.
Figure 3C:
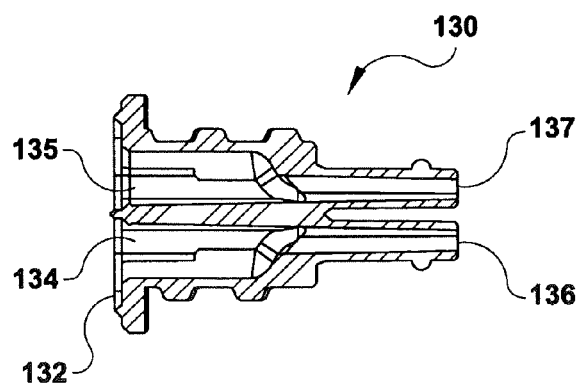
FIG. 3C is a top cross-sectional view taken of the outlet stem of FIG. 3A, taken along line A-A of FIG. 3B.

FIGS. 3A-3D illustrate an embodiment of the outlet stem 130. An outlet stem, in one aspect, is configured to matably attach or mount to a portion of the body 110, such that it overlies the pair of ports defined therein the body. For example and without limitation, the outlet stem can comprise a face portion 132 that is shaped and sized to be received by a recessed portion of the access port body 110. The outlet stem, in one embodiment, comprises a first stem conduit and a second stem conduit 134 and 135, such as illustrated in FIG. 3C, that each extend therethrough the outlet stem from the proximal end to the opposing distal end of the outlet stem. A proximal portion of the outlet stem can, in one embodiment, be threaded, such as shown in FIGS. 3A and 3B. In another aspect, the opposing distal portion of the outlet stem can comprise two prongs 136 and 137. It is contemplated that a respective one of the first and second stem conduits can pass through each of the respective prongs. For example, a first stem conduit 134 can extend from the proximal end, through a first prong 136, to the distal end of the stem. Likewise, a second stem conduit 135 can extend from the proximal end, through a second prong 137, to the distal end of the stem.

In one embodiment, the distal portion of the outlet stem, such as, for example and without limitation, the outlet stem prongs 136 and 137, is configured to matably attach to a dual lumen catheter (not shown), such as those known in the art. Thus, in one aspect, the outlet stem serves as a fluid conduit that is configured to provide fluid communication between each fluid reservoir of the access port body and a respective lumen of a dual lumen catheter.

Figure 4A:
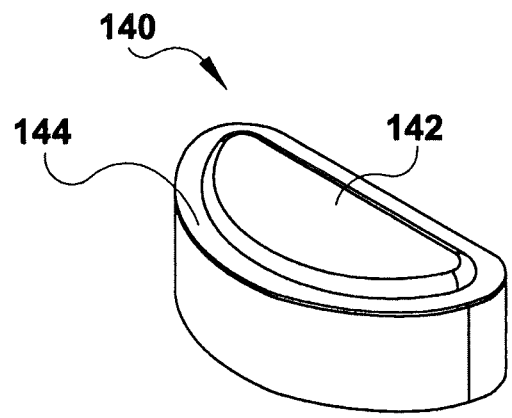
FIG. 4A is a perspective view of a D-shaped septum of an implantable access port, according to one embodiment of the present invention.
Figure 4B:
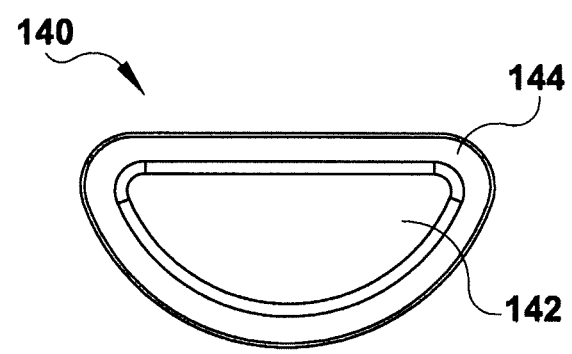
FIG. 4B is a top plan view of the septum of FIG. 4A.
Figure 4C:
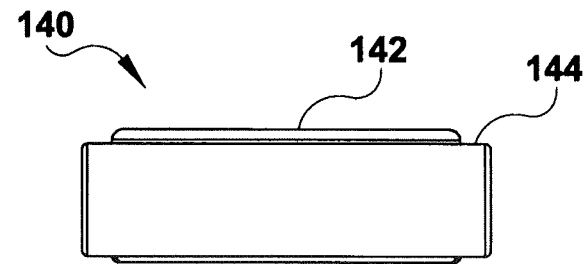
FIG. 4C is a side elevational view of the septum of FIG. 4A.

The septum, according to various embodiments, can comprise a penetrable septum of those types well known in the art. An embodiment of an access port septum 140 is illustrated in FIGS. 4A-4C. In this embodiment, the septum is substantially D-shaped, such as illustrated in FIG. 4B. The periphery of the D-shaped septum can be recessed such as to define a shoulder surface 144 extending along the periphery and to define a raised, D-shaped male protrusion 142, as illustrated in FIG. 4C. When the access port is in an assembled condition, as described further herein below, a portion of the retainer surrounding the respective retainer opening 120 is configured to engage the shoulder surface of the septum.

Figure 5A:
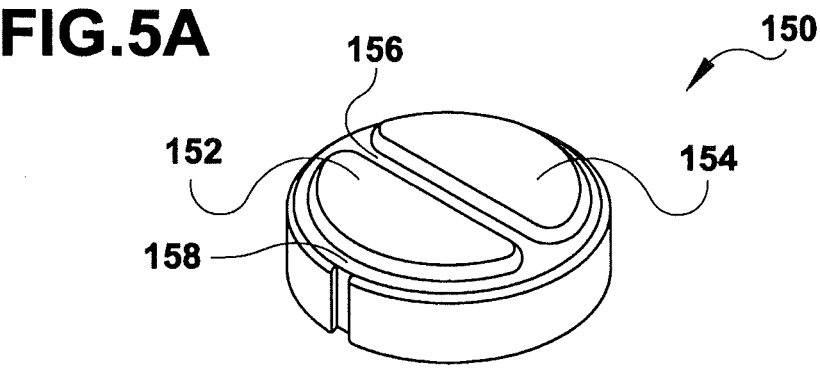
FIG. 5A is a perspective view of a circular septum of an implantable access port having dual D-shaped raised portions, according to one embodiment of the present invention.
Figure 5B:
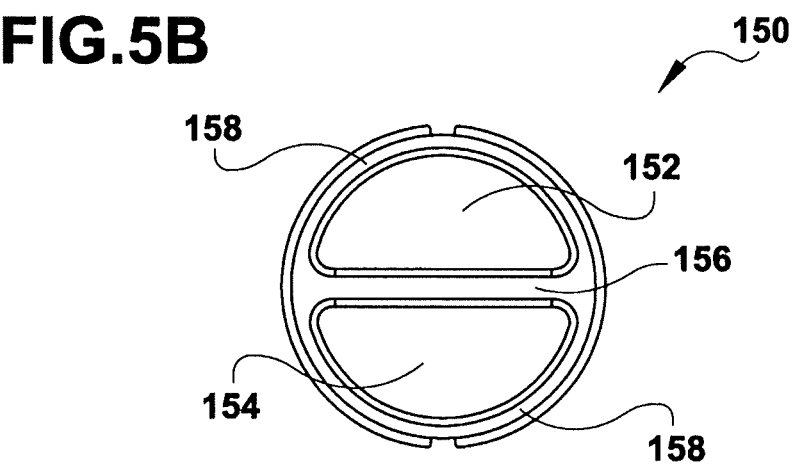
FIG. 5B is a top plan view of the septum of FIG. 5A.
Figure 5C:
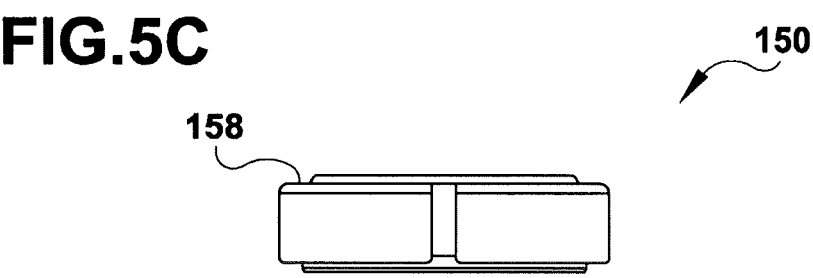
FIG. 5C is a side elevational view of the septum of FIG. 5A.

In another embodiment of the access port septum, the at least one septum can be substantially cylindrical in shape. The septum, in one aspect, has a bottom portion and an opposed top portion. In this embodiment, as illustrated in FIGS. 5A-5C, the bottom portion of the septum defines a first male protrusion and a spaced second male protrusion. In this aspect, the first male protrusion is configured to be sealingly seated within the upper portion of the first reservoir and the second male protrusion is configured to be sealingly seated within the upper portion of the second reservoir.

In one aspect, the respective first and second male protrusions can be substantially D-shaped, or otherwise configured to be received therein the upper portions of the respective first and second reservoirs. In a further aspect, the bottom portion of the septum can define an upper shoulder surface 158, 156 extending about and between the respective first and second D-shaped male protrusions. The upper shoulder surface is configured to sealingly seat against portions of the body when the retainer is connected to the body.

Similarly, the top portion of the septum defines a third male protrusion 152 and a spaced fourth male protrusion 154. In this aspect, at least a portion of the third male protrusion 152 of the septum is configured to be at least partially received therein the first opening of the retainer and at least a portion of the fourth male protrusion 154 is configured to be at least partially received therein the second opening of the retainer.

In one aspect, the respective third and fourth male protrusions can be substantially D-shaped, or otherwise configured to be received therein the respective first and second retainer openings. In a further aspect, it is also contemplated that the top portion of the septum can define a lower shoulder surface 158, 156 extending about and between the respective third and fourth D-shaped male protrusions, which is preferably configured to sealingly seat against portions of the retainer when the retainer is connected to the body.

Figure 6A:
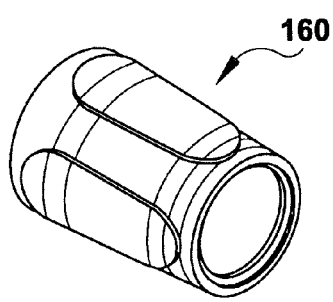
FIG. 6A is a perspective view of a locking sleeve of an implantable access port, according to one embodiment of the present invention.
Figure 6C:
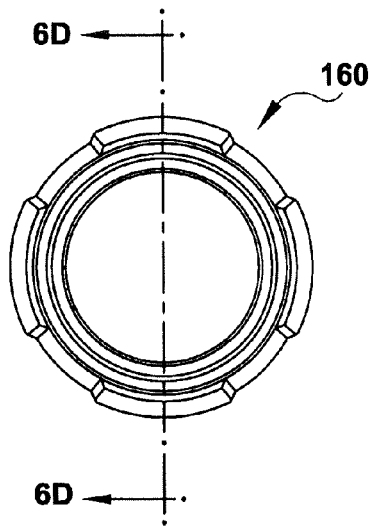
FIG. 6C is a front elevational view of the locking sleeve of FIG. 6A.
Figure 6B:
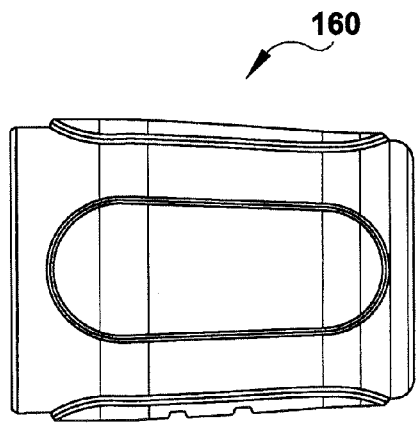
FIG. 6B is a top view of the locking sleeve of FIG. 6A.
Figure 6D:
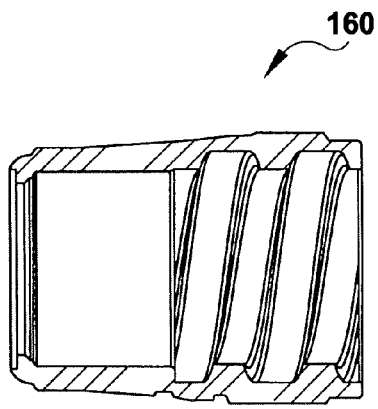
FIG. 6D is a side cross-sectional view of the locking sleeve of FIG. 6A taken along line A-A of FIG. 6C.

FIGS. 6A-6D illustrate an exemplary locking sleeve 160 of an access port. The locking sleeve, in one embodiment, is substantially frusto-conical in shape. The locking sleeve can define an aperture extending therethrough the locking sleeve in a direction substantially parallel to a longitudinal axis of the locking sleeve. Thus, the locking sleeve, in one embodiment, comprises an outer surface and an inner surface. According to a further embodiment, at least a portion of the inner surface can be threaded, such as illustrated in FIG. 6D. As described further below, a locking sleeve can be configured to secure select conventional dual lumen catheters to the outlet stem 130.

FIG. 7A illustrates an exemplary assemblage of an implantable access port. As illustrated, a body 110 is provided, such as described herein with regard to various embodiments. A septum, such as a dual septum 150, can be positioned above the body. In one aspect, the respective first and second d-shaped male protrusions can be positioned to substantially lie above the respective D-shaped first and second reservoirs of the body. Optionally, two separate D-shaped septa 140, such as illustrated in FIGS. 4A-4C can be provided. In this aspect, the respective first and second d-shaped male protrusions can be positioned therein upper portions of the respective D-shaped first and second reservoirs of the body to enclose the minimal amount of space required to allow a hypodermic needle (not illustrated) to access a reservoir through the septum 140 or 150, illustrated in FIGS. 4A-4C or FIGS. 5A-5C, respectively. As described above, the use of two D-shaped reservoirs and the corresponding alignment of the D-shaped portions of the septum, or of individual D-shaped septa, can reduce the geometric footprint of an implantable access port by at least 30%. The illustrated first and second D-shaped reservoirs 112 and 113 allow for the access of a needle that is 14 gauge or larger in size, and the septum 140 is capable of receiving such a needle. The ability of the reservoirs and septum to receive a large needle, such as a 14 gauge needle or larger, is beneficial during apheresis because it allows for optimal blood flow.

Although needles of 14 gauge or larger in size are recognized as being ideally constructed for use in apheresis procedures, the language of this specification should not be construed to limit the types of needles that can be used to practice the invention disclosed by this application. At any point in this specification where a specific needle size is referenced, it is contemplated that a needle of any gauge can be used in the practice of the disclosed invention.

The outlet stem 130 can be connected with the body 110, such as by matably attaching the proximal end of the stem with a portion of the body. FIGS. 7D and 7G illustrate the location of stem conduits 134 and 135, in relation to body 110, when the stem 130 is attached to the body. A retainer 120 can then be positioned over the septum and mounted to the body, thereby securing the septum between the retainer and the body. As discussed above, the retainer can be positioned such that the third and fourth D-shaped male protrusions of the septum substantially lie below a respective D-shaped retainer opening of the retainer. Thus, a portion of the dividing member 126 of the retainer can be positioned within a portion of the lower shoulder surface 156 therebetween the respective third and fourth D-shaped male protrusions of the septum. In this embodiment, the retainer 120 is configured to engage the lower shoulder surface of the septum. Optionally, if two D-shaped septa are provided, each septum can be positioned to substantially lie below a respective D-shaped retainer opening. According to various embodiments, portions of the retainer are configured to engage the landing portions of the one or more septa, thereby securing the septum (a) in place between the retainer and the body.

A gasket 170 can then be positioned over the pronged, distal portion of the stem, and a locking sleeve 160 can be attached to the stem. In one aspect, the threads of the stem can engage the inner threaded portion of the locking sleeve, as is known in the art. A dual lumen catheter can be secured to the stem with the locking sleeve. As described above, when assembled, each of the D-shaped reservoirs of the body can be in fluid communication with a respective lumen of a dual lumen catheter.

According to various embodiments, some or all of the components of an implantable access port can be sized to accommodate the patient in whom the access port will be used, as well as the necessary treatment to be accomplished with the access port. For instance, an access port for use with an adult can be of a larger size than one that is intended for use with a child. This can be especially beneficial for patients undergoing apheresis, such as young children, who may lack adequate peripheral vein access.

In use, a dual reservoir implantable access port can be assembled such as described above. An incision can be made at the implantation site of a patient's body, and the implantable access port can be positioned therein. Because of the reduced geometric footprint of the D-shaped dual reservoir access port, when compared to the geometric footprint of known dual reservoir access ports, a smaller incision can be made at the implantation site of a patient, reducing patient discomfort and other potential medical complications. The access port can be secured at the implantation site with sutures, such as described above. A dual lumen catheter can be fed from the implantation site to the necessary treatment site(s) within the patient's body, and the incision can be closed. In one exemplary aspect, a catheter that has a catheter shaft of at least 10 Fr can be used with the vascular access port. In other exemplary aspects a catheter of 12 Fr or 14 Fr can be used. This is especially beneficial during apheresis because catheters such as these allow for greater blood flow rates.

Figure 11:
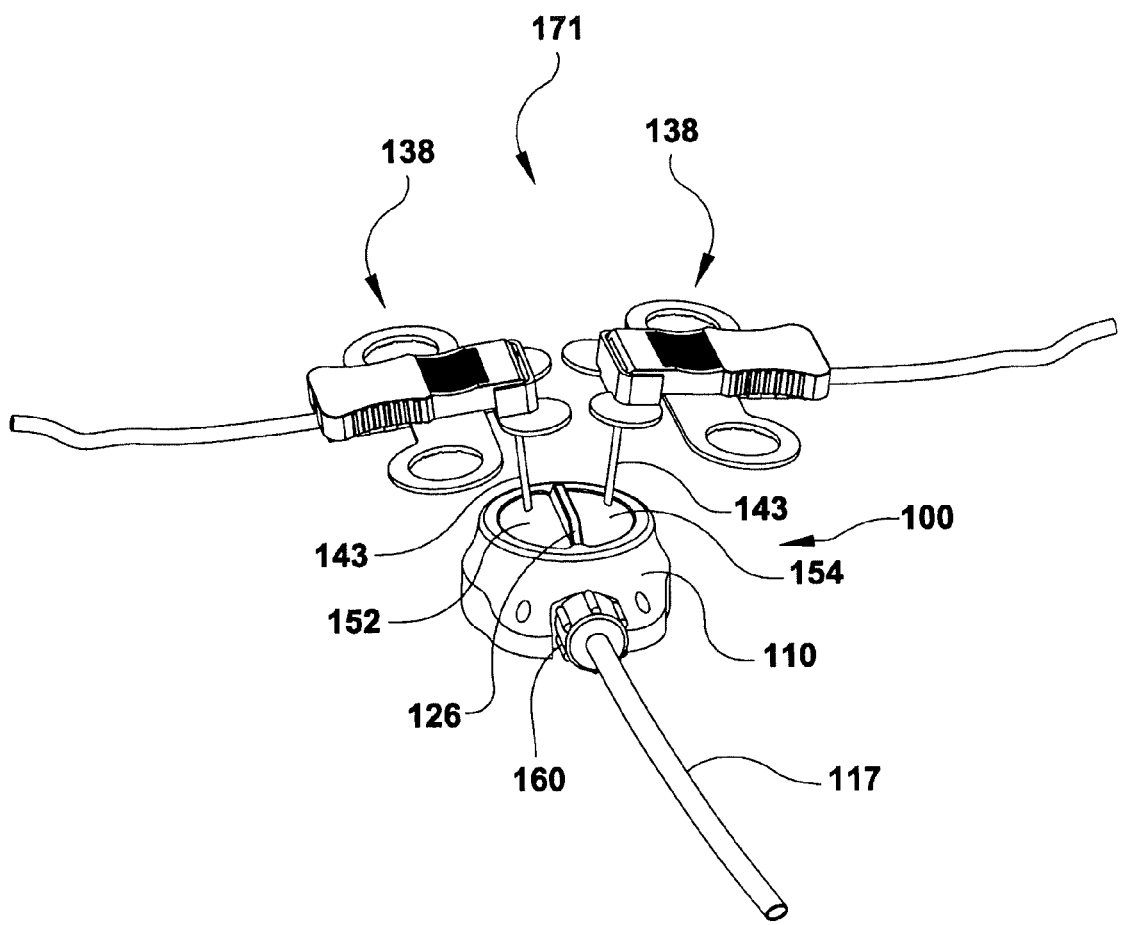
FIG. 11 illustrates one embodiment of the dual reservoir port of FIGS. 1 through 7G, to be used with apheresis, with a needle inserted into each septum of the vascular access port.

When a physician, or other person needing to utilize the access port, needs to administer a treatment and/or draw fluids from the access port, he or she can locate the access port by locating a feature configured to identify the position of the access port (such as a protruding, dividing member 126 of the retainer), as described further herein below. Once the physician has located the protrusion, he or she can access one or both of the D-shaped first and second reservoirs by, for example, injecting a needle through the respective retainer opening, septum, and into the respective reservoir. The physician can then administer treatment to the patient by injecting a fluid into the reservoir; optionally, the physician can draw fluids that have collected in the reservoir from the patient. FIG. 11 illustrates an optimal system 171 for apheresis that comprises a vascular access port 100, as described herein, that allows for maximal flow rates that are desirable for apheresis at any blood viscosity without undue hematocrit, the proportion of blood volume that is occupied by red blood cells. These flow rates are achievable due to the combination of the dual reservoir access port described herein, large bore needles of 14 gauge or larger, and at least a 10 Fr to 12 Fr catheter. In another aspect, a 12 Fr or a 14 Fr catheter can be used.

The manner of fabrication, and materials used in the construction of the implantable access ports 100 of this invention, are as described in U.S. Pat. Nos. 4,673,394, and 5,951,512, each of which is assigned to AngioDynamics, Inc. of Latham, N.Y., and each of which is fully incorporated herein by reference.

For example, and not meant to be limiting, the penetrable septa of the preferred embodiments of this invention can be comprised of a self-resealing polymer, which is preferably an elastomer, such as silicon rubber or a latex, and which is adapted to permit access using a hypodermic needle (not illustrated) into the reservoir formed within the respective access ports. The body and retainer are preferably comprised of a biocompatible material, such as electropolished stainless steel, or other surgical grades of steel, to also include a biocompatible hard material such as titanium. Additionally, the access port, with the exception of the septum, can be manufactured of a suitable plastic material intended for implantation within a human body, and approved for use therefore. Also, the body of the access port, in association with the external opening defined in the side wall of the body, for all embodiments of the inventive access port, are provided with a catheter mount of known construction, which for example, can comprise the locking type of catheter mount illustrated in the '394 patent to Fenton et al., the teaching of which has been incorporated herein by reference.

Further aspects of the present invention are directed generally, to methods and devices associated with the access port having at least one perceivable or identifiable feature for identifying the access port after the access port is implanted within a patient. For example, and not meant to be limiting, at least one or perhaps multiple identifiable feature(s) of an access port contemplated by the instant disclosure can be correlative to information (e.g., a manufacturer's model or design) pertaining to the access port. Thus, an identifiable feature from a particular model of an access port can be unique in relation to at least one of the identifiable features of another model access port.

In varying aspects, it is contemplated that the at least one identifiable feature of an access port can be further correlative with any information of interest, such as type of port, catheter type, manufacturer, date of manufacture, material lots, part numbers, etc. In a further aspect, it is contemplated that once at least one identifiable feature of an access port is observed or otherwise determined, correlation of such at least one feature of an access port can be accomplished, and information pertaining to the access port can be obtained.

As noted above, it is contemplated that the access port of the present invention can comprise at least one feature of the access port that is structured to operatively identify the access port subsequent to subcutaneous implantation. In one exemplary embodiment, the at least one identifiable feature can be perceived by palpation (i.e., to examine by touch), by way of other physical interaction, or by visual observation. In exemplary aspects, that are not meant to be limiting, the at least one feature of the access port can comprise at least one of: a protrusion, such as the protruding dividing member 126 of a retainer, a protruding region, a circumferentially extending protrusion, a recess, a recessed region, a circumferentially extending recess, at least one suture aperture, an overhanging rim feature, a lip feature, an undulation, and/or adjacent features of different elevation.

Optionally, at least a portion of the periphery of the retainer of the access port can include a plurality of protrusions that can be spaced about the periphery as desired. For example, the plurality of protrusions can be symmetrically circumferentially spaced about the periphery. In a varying aspect, the protrusion(s) can be sized, configured, and positioned for forming the at least one identifiable feature of an access port. In these various embodiments, a person of interest can touch or feel the access port through the skin to perceive at least one identifying feature of the implanted access port.

It is also contemplated that the identifiable feature of the access port, such as the exemplary protrusion(s) can be structured for facilitating comfort of a patient within which the access port is implanted. Further, the overall geometry of the access port can be shaped such that the overall general shape of the access port can act as the at least one identifiable feature. It is contemplated that any geometric shape and/or geometric design could be implemented in the general exterior surface shape of the access port such that the shape and/or design could function as an identifiable feature.

In another embodiment, the at least one identifiable feature can be perceived via x-ray or ultrasound imaging. For example, the at least one identifiable feature can comprise a marking on the access port that is formed of material that is visible under application of x-ray or ultrasound technology. In an optional aspect, the at least one identifiable feature can comprise a marking therein the access port that is formed of material that is visible under application of x-ray or ultrasound technology. In this aspect, the "identifiable feature" may not be observable visually or by palpation but, rather, can be otherwise observable via conventional imaging technology such as x-ray or ultrasound.

Figure 9:
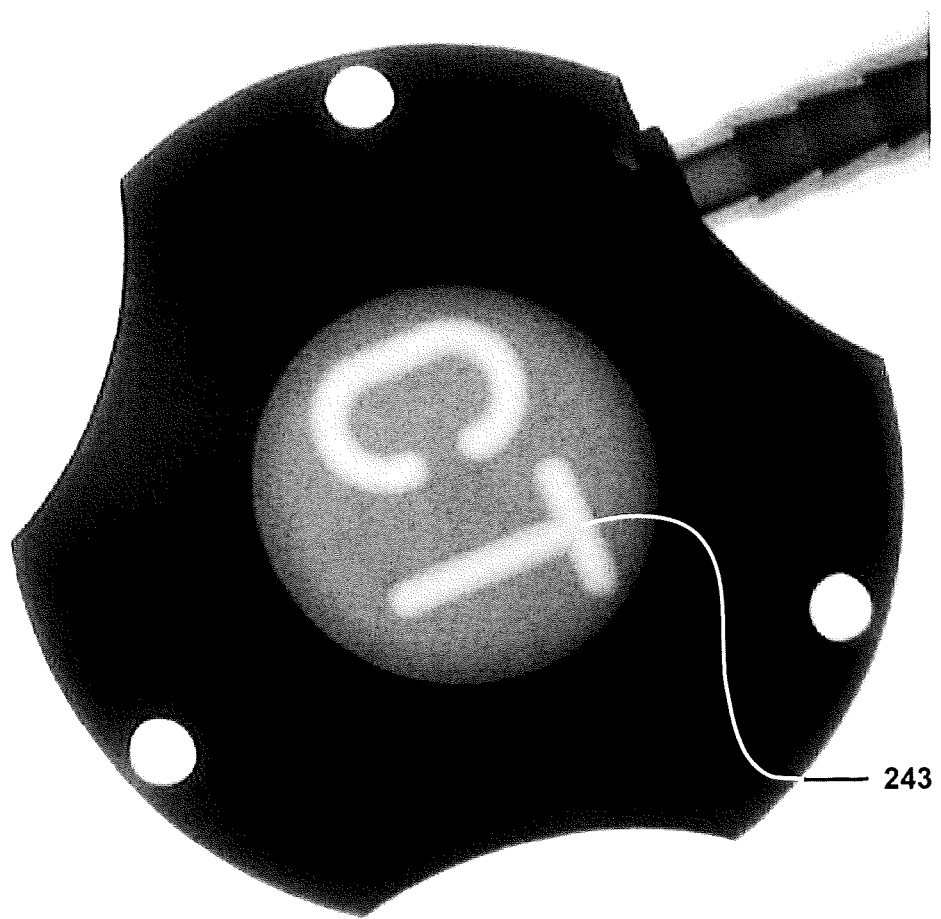
FIG. 9 illustrates an additional embodiment of the bottom surface of the dual reservoir implantable access port with indicia on the bottom of the port indicating CT injectability of the port.

For example, in one embodiment, a metalized feature (e.g., a plate or other metal geometry) can be included by an access port contemplated by the instant disclosure. As may be appreciated, such a metal feature can be represented on an x-ray generated by exposure of the access port to x-ray energy while simultaneously exposing x-ray sensitive film to x-ray energy passing through the access port. Further, the present invention contemplates that a size, shape, or both size and shape of a metal or metalized feature of an access port can be configured for enhancing identification of an access port, i.e., for identifying an implanted access port as a CT port that is suitable for power injection. In one non-limiting example, the base of the port can have a scallop-shaped profile for indicating CT injectability, such as illustrated in FIG. 9.

In one exemplary aspect of the CT identified access port, a portion of the access port, such as the bottom side opposite the septum of the access port, is marked with a "CT" lettering that is visible under radiological conditions. In one exemplary aspect, the port can be made of titanium, in which the letters "CT" are etched into the bottom side of the port, and can act as an identifying means 243, as illustrated in FIG. 9. As can be appreciated, any means for identifying the port can be etched into the bottom side of the port, including one or more alphanumeric characters, one or more symbols, or other identifying means. As shown in FIG. 9, the absence of titanium material in portions of the bottom surface of the port creates an enhanced contrast under radiological conditions, under which the letters can be more visible. In one exemplary aspect, the letters (or other identifying means) can be etched into the bottom of the port using a machine engraving process. In one exemplary aspect, the letters can be etched at a depth of from about 0.010 inches to about 0.020 inches from the surface of the bottom of the port. In one aspect, the letters can be etched into the bottom of the port at a depth of approximately 0.015 inches from the surface of the bottom of the port, equal to approximately half the thickness of the wall of the port, or approximately 0.030 inches.

In another exemplary aspect, and not meant to be limiting, the desired letters could be formed from platinum wire, such as 0.010" thick platinum wire, which can be adhered to the bottom side of the access port with an adhesive, such as a silicone adhesive. Alternatively, the letters can be made from a tungsten filled room temperature vulcanizing (RTV) silicone rubber that are cast and then adhered to the back of the port with an adhesive, such as a silicone adhesive. In another exemplary example, the bottom side of the port could be engraved to form the "CT" lettering and then the engraving could be filled with a tungsten filled RTV silicone. One skilled in the art will appreciate that the RTV silicone rubber has long been used in the medical device industry both as an adhesive and as a base compound.

Figure 13:
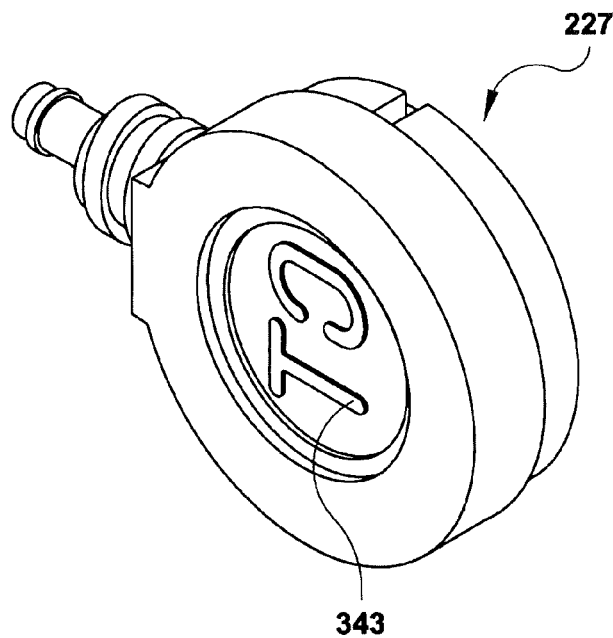
FIG. 13 is a perspective view of an access port having exemplary identification means marked on a bottom surface thereof.
Figure 14:
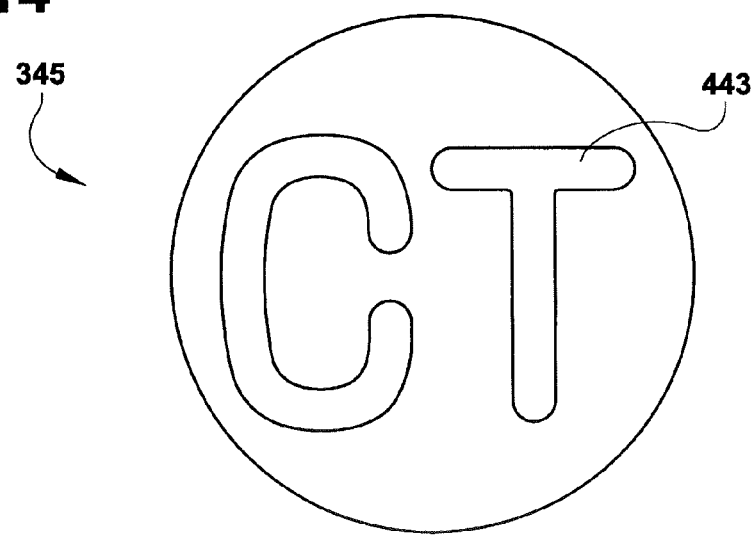
FIG. 14 is a bottom elevational view of a disk for insertion therein an exemplary access port, having identification means marked on a bottom surface thereof the disk.
Figure 15:
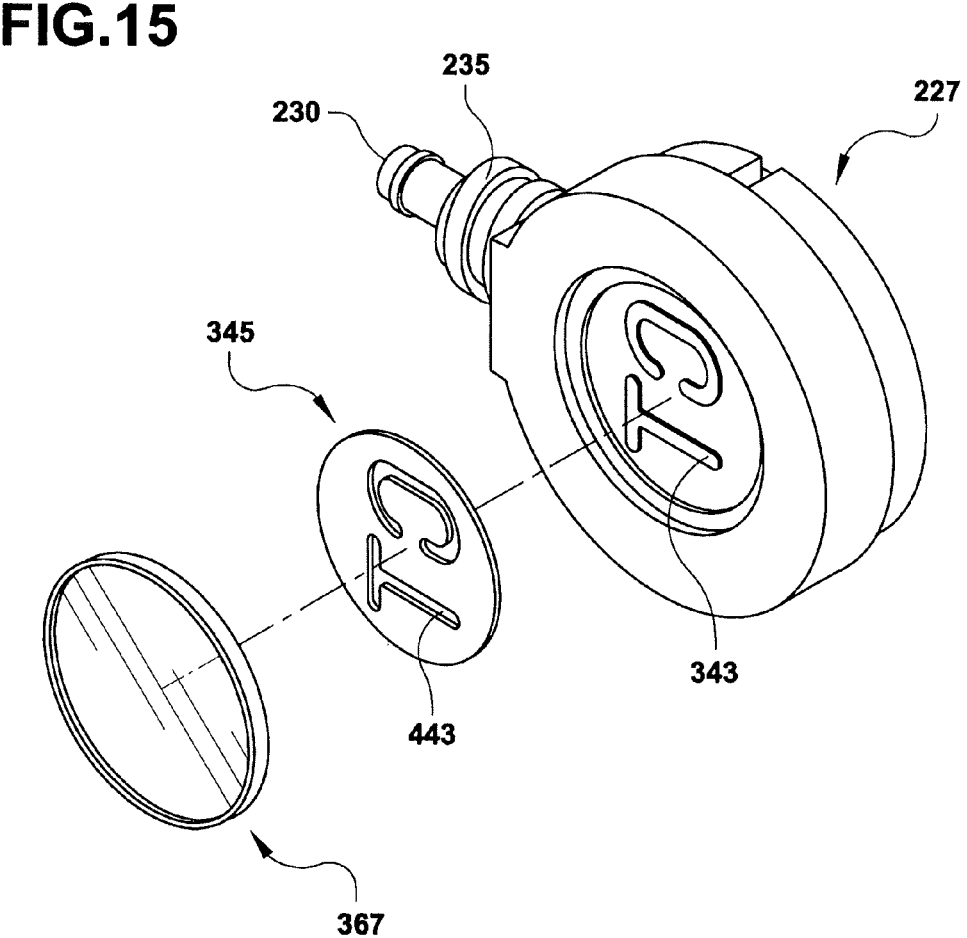
FIG. 15 is an exploded view of the access port of FIG. 13.

According to yet another aspect, such as shown in FIGS. 13 through 15, identifying means 343 (such as the letters "CT") can be carved out of the bottom surface of the port. In one exemplary aspect, the letters "CT" may be raised letters in relation to the bottom surface of the port. In one exemplary aspect, the "CT" letters may be etched out of the bottom of the surface using a process similar to the machine engraving process, as described above. In one exemplary aspect, the bottom surface of the port can have no "CT" letters carved from the bottom surface. In one aspect, the "CT" letters are positioned therein the center of a first circular recessed portion defined therein the bottom surface of the port. A second recessed portion circumferentially surrounds the first recessed portion. The first recessed portion is defined therein the bottom surface of the port surface at a greater recess depth, compared to the second recessed portion that circumferentially surrounds the first recessed portion. In one aspect, the first recessed portion is approximately 0.031 inches from the bottom surface of the port, while the second recessed portion may be approximately 0.021 inches from the bottom surface of the port. In one aspect, the diameter of the first recessed portion is approximately 0.450 inches. In another aspect, the diameter of the second recessed portion is approximately 0.513 inches. In one aspect, the overall diameter of the bottom of the port may be approximately 0.825 inches. The above referenced dimensions for the respective first and second recessed portions are merely exemplary and are not meant to be limiting.

In one aspect, as illustrated in FIGS. 13 and 14, a disk 345 is etched through using a machine engraving process, such that an absence of a portion of the disk material is created, thereby forming the letters "CT". As illustrated in FIG. 15, in one aspect, the disk 345 is then inserted therein the first recessed portion of the port and adhered thereto. In one exemplary aspect, in the assembled configuration, the outer surface of the disk 345 may lie flush with the raised "CT" letters from the first recessed portion, if the "CT" letters are raised in relation to the bottom surface of the port. In one aspect, the disk 345 may be composed of titanium. In another aspect, the disk 345 may be composed of any suitable biocompatible material. As can be appreciated, any means for identifying the port can be etched into or carved from the bottom side of the port, including one or more alpha-numeric characters, one or more symbols, or other identifying means, as described above. In one aspect, the outer diameter of the disk 345 is approximately 0.440 inches. In one aspect, the width of the "CT" letters may be approximately 0.440 inches. In one aspect, the width of the "CT" letters may be approximately 0.346 inches, and the height of the "CT" letters may be approximately 0.237 inches. In one aspect, the thickness of the disk 345 is approximately 0.010 inches. The above referenced dimensions for the width of the letters are merely exemplary and are not meant to be limiting.

In one aspect, as illustrated in FIG. 15, a plastic cap 367 is then inserted on top of the disk 345, such that the outer surface of the plastic cap becomes flush with the bottom surface of the port. In one aspect, the plastic cap 367 has a first portion which is configured to fit into the first recessed portion of the bottom surface of the port, and a second portion which is configured to fit into the second recessed portion of the bottom surface of the port. In one aspect, the plastic cap 367 can have an outer diameter of approximately 0.510 inches and an inner diameter of approximately 0.489 inches. In one aspect, the plastic cap 367 may have a depth of approximately 0.035 inches. Of course, the above referenced dimensions for the plastic cap are merely exemplary and are not meant to be limiting.

In the exemplary examples described above, tungsten was representatively selected as it is readily available and has been used in many medical applications. Further, if the port is made of titanium, selecting tungsten allows the lettering to be more visible under radiology conditions as tungsten is denser than the titanium. However, one would appreciate that it is contemplated that other biocompatible dense metals could comprise at least a portion of a metalized letter.

In one exemplary aspect, the tungsten that is mixed in the silicone rubber RTV can be about 25-micron particle size. One skilled in the art will appreciate that, before vulcanization (cure), RTV is a relatively soft paste with the consistency similar to yogurt. The tungsten can be mixed at relative high concentrations by weight between about 100 to 500 percent by weight, and preferably between about 150 to 400 percent by weight.

In another example, the identifiable feature of the access port can be configured for detection via ultrasound interaction. In one exemplary aspect, such an identifiable feature can comprise an exterior topographical feature. In another aspect, such an identifiable feature can comprise a composite structure including two or more materials that form an interface surface that can be identified by ultrasound imaging. In yet a further embodiment, the at least one identifiable feature can be perceived through magnetic, light, or radio energy interaction or communication with the access port. In this aspect, it is contemplated that the at least one identifiable feature comprises a passive RFID tag that is configured to operate without a separate external power source and to obtain operating power from a reader located external to the subject. Exemplary passive RFID tags are typically programmed with a unique set of data (usually 32 to 128 bits) that cannot be modified. Read-only tags can operate as an identifier comparable to linear barcodes that can contain selected product-specific information. In an alternative aspect, the at least one identifiable feature of an access port can be correlative with the access port being power injectable or for indicating that the port and/or system are capable of being used for apheresis. In this aspect, it is contemplated that the at least one identifiable feature of the access port can be configured to identify the access port as being power injectable subsequent to subcutaneous implantation.

In yet another aspect, the at least one identifiable feature of the access port can be configured to identify the access port as being compatible for use with apheresis or pheresis-style procedures. The procedure of implanting the port involves making an incision in the chest and then forming a pocket distally to the incision for placement of the port body. An incision can be made in the neck of a patient at the point of incision into the internal jugular (IJ) vein where the catheter is to be introduced. A tunnel can then made under the skin using a tunneling device from the incision into the chest to the incision in the neck. The catheter can then be advanced under the skin through this formed tunnel and into an incision made in the IJ. The catheter can then be advanced down the IJ and into the right atrium. Because the port has a detached catheter, the proximal end of the catheter can then be cut and connected to the port body, as described in the typical manufacturer's instructions.

After the port is implanted under the patient's skin, apheresis can be conducted using the system 171 disclosed in FIG. 11. The system disclosed in FIG. 11 comprises the dual reservoir access port 100 disclosed herein and illustrated in FIGS. 1-7G. As also illustrated in FIG. 11, the port 100 comprises septa 152, 154, housing 11 with dividing member 126, locking sleeve 160, and at least one needle 143 that is a 14 gauge or larger size needle. In one exemplary aspect, the needle 143 can be 14 gauge to 22 gauge in size. In one exemplary aspect, the needle can be 18 gauge to 22 gauge in needle size and can be part of a safety infusion set 138, such as that illustrated in FIG. 11.

The system 171 described herein also comprises at least one short bevel Huber point minimally invasive needle 143 that is joined to the infusion set 138. The Infusion sets 138 and needles 143 that are used with system 171 described herein are designed to support the minimum flow rate requirements for apheresis. These infusion sets 138 and needles 143 provide for optimal flow rate generation. The system 171 can be used with a dual lumen double-D catheter with a 12 Fr staggered tip. While such catheters are well known in the art, using the dual reservoir access port described herein, in combination with the needles and catheters also described herein, helps to generate appropriate flow rates while minimizing pressure and hemolysis. In an alternative aspect, the vascular access port 100 described herein can also be used with a triple lumen catheter.

In one exemplary aspect, the infusion set that is used with the vascular access port 100 described herein can be a Life-Guard® safety infusion set (U.S. Pat. No. 6,676,633, incorporated herein by reference). The system 171 also comprises a dual or triple lumen catheter with at least a 10 French (Fr) catheter shaft 117 (a partial portion of which is shown in FIG.

11). In one exemplary aspect the catheter shaft 117 that is used with the vascular access port is from 10 Fr to 14 Fr. In another exemplary aspect, the catheter shaft 117 that is used with the system 171 is between approximately 12 Fr to 14 Fr.

The port 100 described herein is configured for use with adults, as well as pediatric patients in many cases. The size of the vascular access port 100 described herein is constrained to minimize invasiveness of the device. The reservoir and outlet of the port 100 are designed such that pressure constraints are minimized in order to provide for optimal flow rates.

Figure 10:
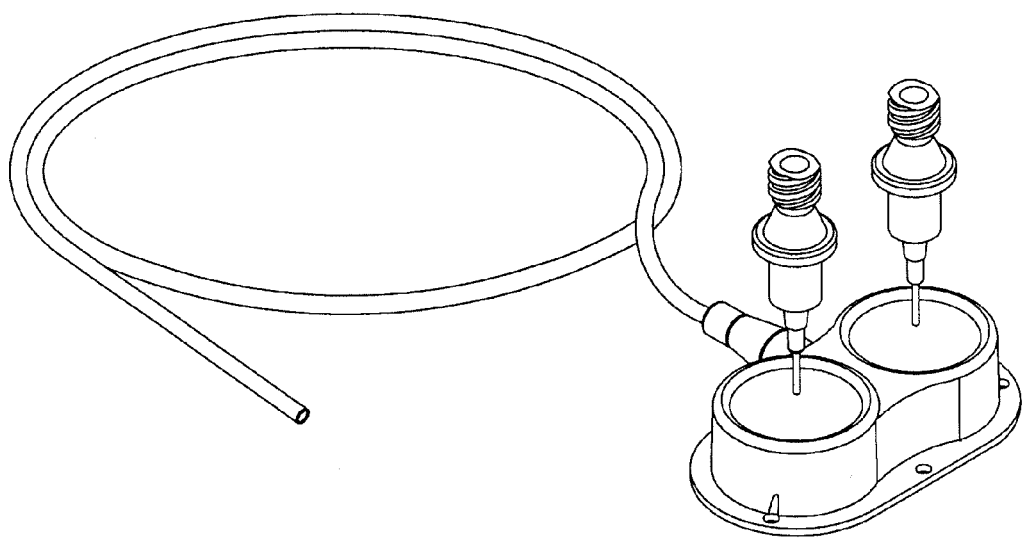
FIG. 10 illustrates a dual reservoir implantable access port known in the art, used in apheresis, and comprising two side-by-side circular reservoirs with a needle inserted into each septum.
Figure 12:
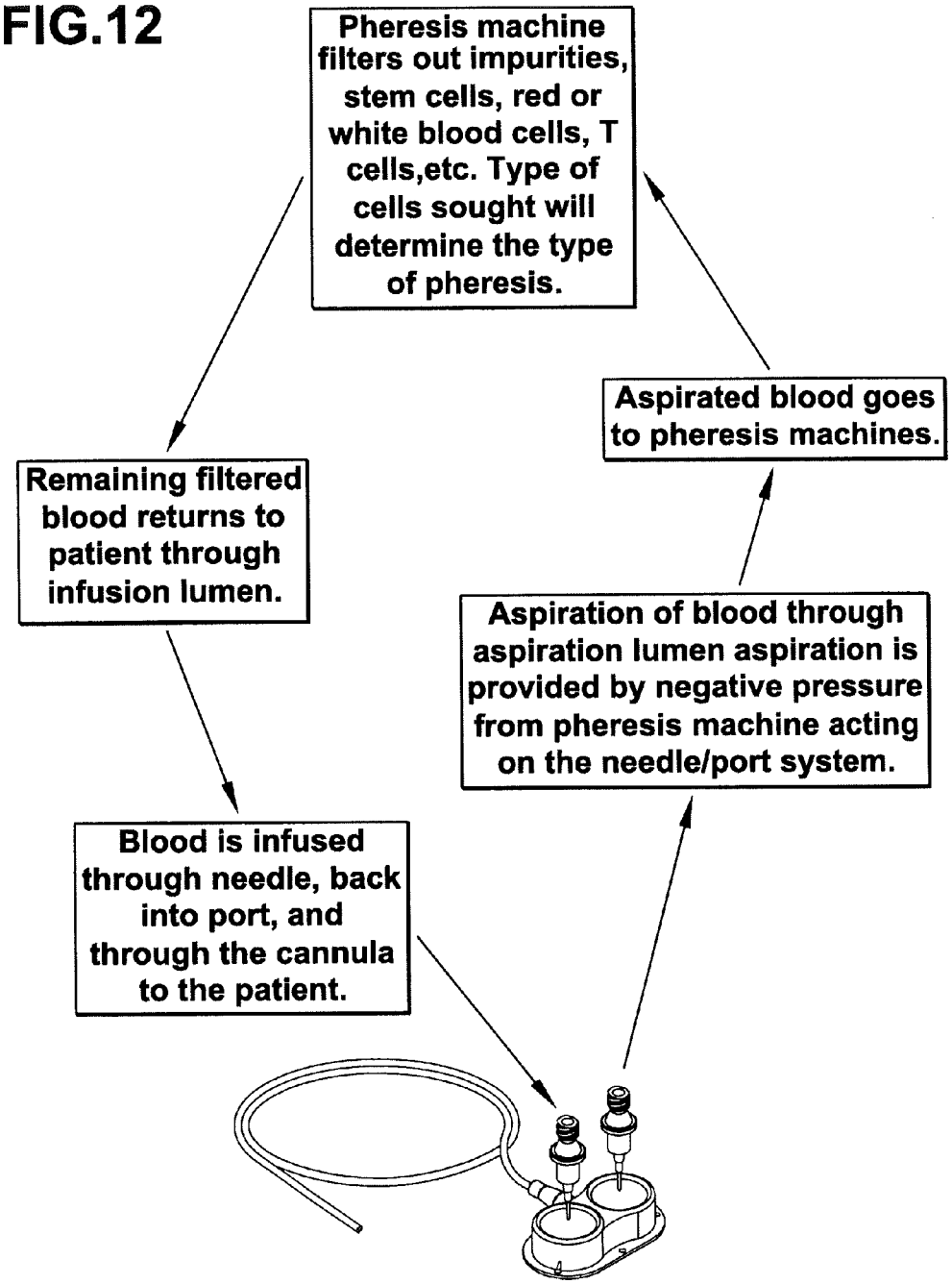
FIG. 12 is a schematic illustration of a dual reservoir implantable access port being used in an apheresis procedure.

To perform any apheresis procedures using the port 100 disclosed herein, the port 100 is accessed with a 14 gauge or larger needle, as illustrated in FIG. 11. After the dual reservoir port 100 is accessed using a 14 gauge or larger non-coring needle, the patient can then be connected to an apheresis machine. During the apheresis procedure, as illustrated in the flow chart illustrated in FIG. 12, blood is aspirated through one aspiration lumen of a vascular access catheter. Although the apheresis process is illustrated herein using a conventional dual reservoir port, such as that illustrated in FIG. 10, the apheresis process can be used with any dual reservoir vascular access port, such as the dual reservoir access port 100 disclosed herein.

The aspiration is provided by negative pressure from a pheresis machine acting on the needle of the system 171. The aspirated blood then goes to the pheresis machine. During the pheresis procedure, the pheresis machine filters out impurities, including stem cells, red or white blood cells, or T cells, for example. The type of cells sought determines the type of pheresis that will be performed—for example, plasmapheresis, plateletpheresis, photopheresis, erythropheresis, and erythrocytapheresis (RCX). The remaining filtered blood returns to the patient through the infusion lumen of the catheter. Blood is then infused through the needle, back into the port, and through a cannula to the patient. After apheresis, the ports are then flushed with ten milliliters of normal saline and heparin. This also helps prevent clotting within the catheter. Using the vascular access port system 171 described herein in pediatric patients has been successful in achieving blood flow rates of between 30 and 45 milliliters/minute and maximum pressures below 125-150 for draw and 50-100 for return. The system 171 provided herein allows for optimal flow rates for apheresis. The flow rates allow for decreased Hgb S (abnormal hemoglobin) levels and decreased iron load. This system 171 allows the safe performance of apheresis on children and adults who cannot benefit from simple transfusions and have poor peripheral access, and also allows less time spent in the outpatient unit.

Although several embodiments of the invention have been disclosed in the foregoing specification, it is understood by those skilled in the art that many modifications and other embodiments will come to mind to which the invention pertains, having the benefit of the teaching presented in the foregoing description and associated drawings. It is thus understood that the invention is not limited to the specific embodiments disclosed hereinabove, and that many modifications and other embodiments are intended to be included within the scope of the invention. Moreover, although specific terms are employed herein, they are used only in a generic and descriptive sense, and are not intended to be limiting.

What is claimed is:

1. An implantable vascular access port comprising:
  a first reservoir having a first opening extending to a top surface of the port, the first opening fluidly sealed by a first septum, and a first outlet in fluid communication with the first reservoir; and
  a second reservoir having a second opening extending to the top surface of the port, the second opening fluidly sealed by a second septum, and a second outlet in fluid communication with the second reservoir;
  wherein the first and second reservoir are separated by and adjacent to a common wall, the common wall having a first end portion, a second end portion, and an intermediate portion between the first and second end portions,
  wherein each of the first and second reservoirs include a curved side surface,
  wherein the first and second end portions of the common wall intersect the curved side surfaces of the first and second reservoirs to form rounded corners,
  wherein the first outlet is defined proximate the rounded corner of the first reservoir,
  wherein the second outlet is defined proximate the rounded corner of the second reservoir,
  wherein the first and second opening comprise edges of the common wall at a top surface of the port, the edges at the intermediate portion being substantially parallel to a common linear axis, and
  wherein the first and second septums are disposed on opposite sides of the common linear axis; and
  an access port retainer comprising a first retainer opening and a second retainer opening, the first retainer opening and the second retainer opening having an opposing D-shaped configuration, the first retainer opening and second retainer opening being separated by a dividing member that is aligned with the reservoir common wall, tire first retainer opening overlaying the second reservoir; and
  a substantially circular footprint.

2. The implantable vascular access port of claim 1 further comprising the first and second reservoir having opposing D-shaped configuration.

3. The impassable vascular access port of claim 1 further comprising: the first and second septum having an opposing D-shaped configuration.

4. The implantable vascular access port of claim 3, further comprising: the first septum and the second septum being needle penetrable and aligned between the first reservoir and second reservoir and the first retainer opening and second retainer opening.

5. The implantable vascular access port of claim 3, further comprising: the septum having a lower shoulder surface extending about and between the first septum and second septum and aligned with the retainer dividing member and reservoir common wall.

6. The implantable vascular access port of claim 1, wherein the top surface of the port has a substantially circular profile.

7. An implantable vascular access port, comprising:
  a first reservoir having a first opening extending to a top surface of the port, the first opening fluidly sealed by a first septum, and a first outlet in fluid communication with the first reservoir; and
  a second reservoir having a second opening extending to the top surface of the port, the second opening fluidly sealed by a second septum, and a second outlet in fluid communication with the second reservoir;
  wherein the first and second reservoir are separated by and adjacent to a common wall, and
  wherein the first and second septums have an opposing D-shaped configuration; and
  an access port retainer comprising a first retainer opening and a second retainer opening, the first retainer opening and the second retainer opening having an opposing D-shaped configuration, the first retainer opening and second retainer opening being separated by a dividing, member that is aligned with the reservoir common wall, the first retainer opening substantially overlaying the first, reservoir and the second retainer opening substantially overlaying the second reservoir; and
a substantially circular footprint.

8. The implantable vascular access port of claim 7 further comprising: the first and second reservoir having an opposing D-shaped configuration.

9. The implantable vascular access port of claim 7, herein the top surface of port substantially circular profile.

* * * * *